(12) United States Patent
Jaramaz et al.

(10) Patent No.: US 10,420,611 B2
(45) Date of Patent: Sep. 24, 2019

(54) COMPUTER-AIDED PROSTHESIS ALIGNMENT

(71) Applicant: BLUE BELT TECHNOLOGIES, INC., Pittsburgh, PA (US)

(72) Inventors: Branislav Jaramaz, Pittsburgh, PA (US); Constantinos Nikou, Monroeville, PA (US)

(73) Assignee: Blue Belt Technologies, Inc., Pittsburgh, PA (US)

( * ) Notice: Subject to any disclaimer, the term of this patent is extended or adjusted under 35 U.S.C. 154(b) by 14 days.

(21) Appl. No.: 15/123,700

(22) PCT Filed: Mar. 4, 2015

(86) PCT No.: PCT/US2015/018711
§ 371 (c)(1),
(2) Date: Sep. 6, 2016

(87) PCT Pub. No.: WO2015/134592
PCT Pub. Date: Sep. 11, 2015

(65) Prior Publication Data
US 2017/0014189 A1    Jan. 19, 2017

Related U.S. Application Data

(60) Provisional application No. 61/948,102, filed on Mar. 5, 2014.

(51) Int. Cl.
*A61B 34/10* (2016.01)
*G16B 5/00* (2019.01)
*A61B 34/00* (2016.01)

(52) U.S. Cl.
CPC ............... *A61B 34/10* (2016.02); *G16B 5/00* (2019.02); *A61B 34/25* (2016.02); *A61B 2034/104* (2016.02); *A61B 2034/105* (2016.02)

(58) Field of Classification Search
CPC .............. A61B 34/10; A61B 2034/104; A61B 2034/105; A61B 34/25; G06F 16/12
(Continued)

(56) References Cited

U.S. PATENT DOCUMENTS

| | | |
|---|---|---|
| 5,086,401 A | 2/1992 | Glassman |
| 5,408,409 A | 4/1995 | Glassman et al. |

(Continued)

FOREIGN PATENT DOCUMENTS

| | | |
|---|---|---|
| WO | 2013049534 A1 | 4/2013 |
| WO | 2015134592 A1 | 9/2015 |
| WO | 2017106294 A2 | 12/2017 |

OTHER PUBLICATIONS

Schnmutz_2008 (2008) Fit Assessment of Anatomic Plates for the Distal Medial Tibia. Journal of Orthopaedic Trauma 22(4):pp. 258-263.*

(Continued)

*Primary Examiner* — Brian S Cook
(74) *Attorney, Agent, or Firm* — Pepper Hamilton LLP (57) ABSTRACT

Systems and methods for computer-aided alignment and positioning of a prosthesis component onto a target host bone, such as in joint resurfacing arthroplasty, are discussed. A system for can include a processor unit and a user interface unit. The processor unit can receive a target bone model including a first data set representing a target bone surface, and a prosthesis model including a second data set representing a prosthesis surface. The prosthesis, when positioned against the target bone, is configured to at least partially replace the articulation surface. The processor unit can generate an articulation interface representation that indicates spatial misalignment between one or more portions of the prosthesis surface and one or more portions of the (Continued)

target bone surface when the prosthesis model is positioned against the target bone model.

32 Claims, 6 Drawing Sheets

(58) Field of Classification Search
USPC .............................................................. 703/7
See application file for complete search history.

(56) References Cited

U.S. PATENT DOCUMENTS

| | | | |
|---|---|---|---|
| 6,205,411 B1* | 3/2001 | DiGioia, III | G06F 19/00 703/11 |
| 7,559,931 B2 | 7/2009 | Stone | |
| 9,585,725 B2 | 3/2017 | Bonutti | |
| 9,665,686 B2 | 5/2017 | Van Vorhis et al. | |
| 9,684,768 B2 | 6/2017 | Lavalee et al. | |
| 2003/0153978 A1 | 8/2003 | Whiteside | |
| 2008/0033571 A1 | 2/2008 | Tuke | |
| 2009/0043556 A1 | 2/2009 | Axelson | |
| 2009/0209851 A1* | 8/2009 | Blau | A61B 17/1703 600/426 |
| 2012/0271599 A1* | 10/2012 | Lavallee | G06F 19/3437 703/1 |
| 2012/0276509 A1* | 11/2012 | Iannotti | G09B 23/30 434/267 |
| 2013/0144392 A1 | 6/2013 | Hughes | |

OTHER PUBLICATIONS

Sreng_2006, Using Visual Cues of Contact to Improve Interactive Manipulation of Virtual Objects in Industrial Assmebly/ Maintenance Simulations, IEEE Transactions on Visualization and Computer Graphics, vol. 12, No. 5, Sep./Oct. 2006.*

Schnmutz_2008 (2008) Fit Assessment of Anatomic Plates for the DistalMedial Tibia. Journal of Orthopaedic Trauma 22(4):pp. 258-263 2009 (2009).*

Sreng_2006, Using Visual Cues of Contact to Improve Interactive Manipulation of Virtual Objects in Industrial Assmebly/ Maintenance Simulations, IEEE Transactions on Visualization and Computer Graphics, vol. 12, No. 5, Sep./Oct. 2006 (2006).*

Chao et al. "Simulation and Animation of Musculosketal Joint System" (Nov. 1, 1993) J. Biomechanical Engineering 115(4B): 562-568.

Chinese Office Action for CN20130058810.6 dated Feb. 6, 2017.

Chinese Office Action for CN201480027135.5 dated Jan. 17, 2017.

Delp et al. "An Interactive Graphics-Based Model of the Lower Extremity to Study Orthopaedic Surgical Procedures" (Aug. 1990) IEE Transactions on Biomedical Engineering 37(8): 757-767.

DiGioia et al. "An Integrated Approach to Medical Robotics and Computer Assisted Surgery in Orthopaedics" (1995) Carnegie Mellon University 106-111.

DiGioia et al. "HipNav: Pre-operative Planning and Intra-operative Navigational Guidance for Acetabular Implant Placement in Total Hip Replacement Surgery" (Nov. 1995) Preceedings of CAOS '96 1-8.

Harris et al. "Experiences with Robotic Systems for Knee Surgery" (Mar. 19-22, 1997) Springer-Verlag, London, UK 757-766.

Freysinger et al. "A Passive-Marker-Based Optical System for Computer-Aided Surgery in Otorhinolaryngology: Development and First Clinical Experiences" (Feb. 2002) The Laryngoscope 112(2):409.

O'Toole III et al. "Towards More Capable and Less Invasive Robotic Surgery in Orthopaedics" (1995) Computer Vision, Virtual Reality and Robotics in Medicine 905: 123-130.

Taylor et al. "An Image-Directed Robotic System for Precise Orthopaedic Surgery" (Jun. 1994) Iee Transactions on Robotics and Automation 10 (3): 261-275.

Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.

International Search Report and Written Opinion for PCT/US2015/018711 dated Jun. 17, 2015.

* cited by examiner

COMPUTER-AIDED PROSTHESIS ALIGNMENT

CLAIM OF PRIORITY

This application is a United States National Phase filing of International Application No. PCT/US15/018711 which claims the benefit of priority of U.S. Provisional Patent Application Ser. No. 61/948,102, filed on Mar. 5, 2014, which is hereby incorporated by reference herein in its entirety.

TECHNICAL FIELD

This document relates generally to computer-aided orthopedic surgery, and more specifically to systems and methods for computer-aided alignment and positioning of a prosthesis onto a bone surface.

BACKGROUND

The use of computers, robotics, and imaging to aid orthopedic surgery is well known in the art. There has been a great deal of study and development of computer-aided navigation and robotics systems used to guide surgical procedures. For example, a precision freehand sculptor employs a robotic surgery system to assist the surgeon in accurately cutting a bone into a desired shape. In interventions such as total hip replacement, computer-aided surgery techniques have been used to improve the accuracy and reliability of the surgery. Orthopedic surgery guided by images has also been found useful in preplanning and guiding the correct anatomical position of displaced bone fragments in fractures, allowing a good fixation by osteosynthesis.

Dysfunctional joints such as hips or knees may require surgical treatment in case of arthritis, avascular necrosis, or other debilitating pathological conditions. Joint resurfacing arthroplasty is a joint replacement procedure where a portion of the joint tissue, such as an articulation surface, is replaced by a resurfacing prosthesis. Joint resurfacing arthroplasty has been found to be a viable alternative to the traditional total joint replacement, such as total knee or total hip replacement, in certain patients particularly younger and active patients with relatively strong bones. As an example, hip resurfacing arthroplasty involves replacing worn cartilage and damaged bone tissue in the acetabulum with a cup-shaped prosthesis liner in the acetabulum. The femoral head can be trimmed and reshaped, and a femoral prosthesis cap can be permanently affixed to the trimmed femoral head. The prosthesis capped femoral head and the acetabular cup can then be reconnected to restore the function of the hip joint.

SUMMARY

Proper positioning of joint resurfacing components can be crucial to the outcome of prosthesis implantation procedures such as joint resurfacing arthroplasty. In hip resurfacing arthroplasty, acetabular cup needs to be properly positioned onto and aligned with the resurfaced acetabulum before the acetabular cup is pressure-fit into the resurfaced acetabulum. Similarly, the femoral cap must be properly aligned to the trimmed host femoral head before the femoral cap can be cemented into the trimmed femoral head. Proper alignment and positioning of resurfacing components onto the respective host bones allows the desirable range and flexibility of joint movement. Malpositioning of prosthesis components, however, can result in impingement, increased rates of dislocation, wear and failure of the prosthesis, among many other complications. In particular, impingement of the femoral neck on the acetabular component of a hip resurfacing may result in femoral neck fracture and loosening of the acetabular component.

Positioning of prosthesis onto a resurfaced target host bone usually requires a surgeon to mentally map and compare the shape, orientation, and relative positions of the prosthesis components and the target bones. Computer-aided tools can be used to assist the surgeon in better aligning the prosthesis components against the target bones. These methods and tools, however, can be difficult to operate and may suffer from lack of reliability and certainty. For example, some surgical areas can have reduced visualization and access, particularly during minimally invasive surgery and arthroscopic techniques. Identifying the misaligned regions on the prosthesis components and/or on the host target bones can be problematic and imprecise due to the interference of surrounding tissues within the surgical area. Determining and visualizing the correct positions and orientations of the prosthesis with respect to the target bone can be practically difficult. Therefore, the present inventors have recognized that there remains a considerable need for systems and methods that can assist the surgeon in reliably positioning the prosthesis onto the target bone with improved accuracy and consistency.

Various embodiments described herein can help improve the accuracy and the reliability in positioning a prosthesis such as a resurfacing component onto a target bone such as a host femur or acetabulum. When integrated within, or used in conjunction with, a robotic surgical instrument, the present systems and methods can improve the patient outcome experiencing an orthopedic procedure. For example, a prosthesis positioning and alignment system can include a processor unit and a user interface unit. The processor unit can receive a target bone model including a first data set representing a target bone surface, and a prosthesis model including a second data set representing a prosthesis surface. The prosthesis is configured to at least partially replace an articulation surface of the target bone. Using the target bone surface representation and the prosthesis surface representation, the processor unit can generate an articulation interface representation that indicates spatial misalignment between one or more portions of the prosthesis surface and one or more portions of the target bone surface when the prosthesis model is positioned against the target bone model. The user interface can include a user input module that receives an indication of a change in position of the target bone model or the prosthesis model. The user interface also includes a display module that can display one or more of the target bone model, the prosthesis model, and the articulation interface representation.

A method embodiment for aligning a prosthesis surface to a target bone surface can comprise the operations of receiving a target bone model which includes a data set representing a target bone surface, a prosthesis model which includes a data set representing a prosthesis surface, and an indication of a position of the target bone model relative to a position of the prosthesis model. The method also comprises generating an articulation interface representation, which is indicative of one or more portions of the prosthesis surface being spatially misaligned with one or more portions of the target bone surface when the two models are positioned against each other at certain locations and orientations. One or more of the target bone model, the prosthesis model, and the articulation interface representation can be displayed on a display module to provide feedback to a system user such as a surgeon and assist the system user in properly positioning the prosthesis on the target bone.

A machine-readable storage medium embodiment of the present document can include instructions that, when executed by a machine, cause the machine to receive a target bone model including a first data set representing a target bone surface, a prosthesis model including a second data set representing a prosthesis surface, and an indication of a position of the target bone model relative to a position of the prosthesis model. The machine can be caused to generate an articulation interface representation indicative of one or more portions of the prosthesis surface being spatially misaligned with respective one or more portions of the target bone surface when the two models are positioned against each other at certain positions and orientations. The instructions can also cause the machine to display one or more of the target bone model, the prosthesis model, and the articulation interface representation on a display module to provide feedback to a system user.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices and methods for computer-aided positioning and alignment of a prosthesis component onto a target bone. Various embodiments described herein can help improve the efficacy and the reliability in osteoplasty planning, such as in an orthopedic implant surgery. The methods and devices described herein can also be applicable to planning surgery of pathological bones under various other conditions.

Figure 1:
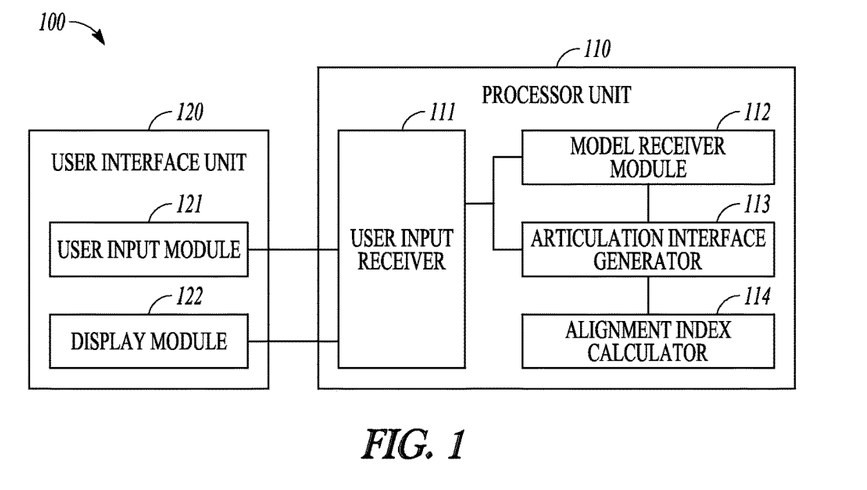
FIG. 1 is a block diagram that illustrates an example of a prosthesis alignment and positioning system.

FIG. 1 is a block diagram that illustrates an example of a prosthesis alignment system 100 for use in an orthopedic surgery on a target bone. The system 100 includes a processor unit 110 and a user interface unit 120. The system 100 can be configured to generate, and present to a system user, a representation of an articulation interface between a prosthesis component and a target bone shaped to host the prosthesis component. The system 100 can also provide the system user with information including degree of alignment between the prosthesis and the target bone.

The processor unit 110 can include a user input receiver 111, a model receiver module 112, an articulation interface generator 113, and an alignment index calculator 114. The user input receiver 111 can receive a target bone model such as a first data set representing a target bone surface. The target bone surface can be an articulation surface of the target bone, such as acetabular surface, a surface of a proximal or distal extremity of a femur, a surface of a proximal or distal extremity of a tibia, or a surface of any other bone in a body. The target bone model can include a medical image, a point cloud, a parametric model, or other morphological description of the target bone. The medical images can include two-dimensional (2D) or three-dimensional (3D) images. Examples of the medical images include an X-ray, an ultrasound image, a computed tomography (CT) scan, a magnetic resonance (MR) image, a positron emission tomography (PET) image, a single-photon emission computed tomography (SPECT) image, or an arthrogram. The target bone model can include shape data, appearance data, or data representing other morphological characteristics of the target bone surface. The shape data may include geometric characteristics of a bone such as landmarks, surfaces, boundaries of 3D images objections. The appearance data may include both geometric characteristics and intensity information of a bone.

The user input receiver 111 can be coupled to the user interface unit 120, such as via a user input module 121, to receive the target bone model. The user input module 121 can receive the target bone model from a patient database. The user input module 121 can alternatively be coupled to an imaging system or other image acquisition module within or external to the system 100. The imagining system or the image acquisition module can feed the target bone model (e.g., one or more images or point clouds) to the system 100 via the user input module 121.

The model receiver module 112 can receive a prosthesis model such as a second data set representing a prosthesis surface. The prosthesis is configured to at least partially replace the articulation surface of the target bone when the prosthesis surface is aligned with the articulation surface. The prosthesis model can include information such as shape or appearance of the prosthesis surface. The prosthesis model can be in a form of a parametric model, a statistical model, a shape-based model, a volumetric model, an elastic model, a geometric spine model, or a finite element model. In some embodiments, the target bone model received from the user input module 121 has data format or modality comparable to the prosthesis model received from the model receiver module 112. For example, the user input module 121 receives a 3D graphical representation such as a medical image of the surface of a femoral head. Accordingly, the model receiver module 112 receives a 3D graphical representation such as a computer-simulated image of the prosthesis surface.

The articulation interface generator 113, coupled to the model receiver module 112 and the user input receiver 111, is configured to generate an articulation interface representation using both the target bone surface representation and the prosthesis surface representation. The articulation interface representation can be indicative of one or more portions of the prosthesis surface being spatially misaligned with one or more portions of the target bone surface when the two models are positioned against each other in specified positions. The articulation interface representation can include a color-coded representation, an annotative representation, or other formats of representations or overlays of two or more different representations. The articulation interface representation provides feedback to the system user such as a surgeon, and assists the system user in properly positioning the prosthesis on the target bone. Examples of the articulation interface generator 113 are discussed below, such as with reference of FIG. 2.

The alignment index calculator 114 can be configured to calculate an alignment index using the articulation interface representation. The alignment index can be a measure of an overall disconformity between the target bone surface and the prosthesis surface. In an example, L can be computed as a square-root of the sum of squared regional similarity measures among all segments, that is:

$$L=\sqrt{\sum_{i=1}^{N}\|X(i),Y(i)\|^2}$$

The alignment index can also include statistical of disconformity measurements among various regions of the articulation interface representation. For example, the alignment index can include maximum, minimum, average, median, range, histogram, or spatial distributions of the disconformities among multiple regions of the target bone surface and the prosthesis surface. The alignment index calculator 114 can further determine that a desirable alignment between the prosthesis surface and the target bone surface has been achieved when the alignment index meets a specified criterion.

The user interface unit 120 can include a user input module 121 and a display module 122. As discussed above, the user input module 121 can receive a target bone model including a representation of the target bone surface and provide the target bone model to the processor unit 110 through the user input receiver 111. The user input module 121 can be communicatively coupled to an external module for generating or storing the target bone model.

The user input module 121 can include one or more pointing devices, such as a mouse, a trackball, or a touch screen, that are connected to the user interface unit 120. The pointing device enables system users to issue user commands to the system 100. For example, the user input module 121 can receive a user command that selectively alters one or more properties of the target bone model or one or more properties of the prosthesis model. Examples of user command includes translating, rotating, reflecting, scaling, stretching, shrinking, or performing any other manipulations or combinations of the manipulations over one or both of the target bone model or the prosthesis model. The user command can also include a plurality of specified angles of views or projections of the target bone model, the prosthesis model, or the articulation interface representation. The user command can further include selection, de-selection, change in position, or change in orientation of either or both of the target bone model and the prosthesis model. In an example, when only one model (either the target bone model or the prosthesis model) is selected and repositioned, the user input module 121 can receive a change of position of the selected model relative to the other model. In another example, when both the target bone model and the prosthesis model are selected, the user input module 121 can receive a concurrent change of positions of both models with preserved relative position between the two models. In response to the user command, the processor unit 110 can update the presentations of target bone model, the prosthesis model, or the articulation interface representation. In an example, the articulation interface generator 113 can re-generate an articulation interface representation if there is a change of relative positions or orientations between the target bone surface representation and the prosthesis surface representation. In another example, the articulation interface generator 113 can perform spatial transformation of the articulation interface representation in response to user command of translating or rotating a model, or projecting a model from a different specified angle.

In some examples, the user input module 121 can receive a command of animating an image sequence of the target bone model, the prosthesis model, or the articulation interface representation. The command of animation can include parameters controlling the speed (e.g., frame rate), direction, and effects of motion of one or both of the models. The animation can show the relative positions or orientations of one model (e.g., the target bone model) with respect to the other model (e.g., the prosthesis model).

The display module 122, coupled to the user input module 121 and the processor unit 110, can be configured to display the target bone model, the prosthesis model, and the articulation interface representation. In an example, the display module 122 can generate an articulation interface representation overlaid with one or both of the target bone model, the prosthesis model. Examples of the display module 122 are discussed below, such as with reference of FIGS. 3A-D and FIGS. 4A-D.

Figure 2:
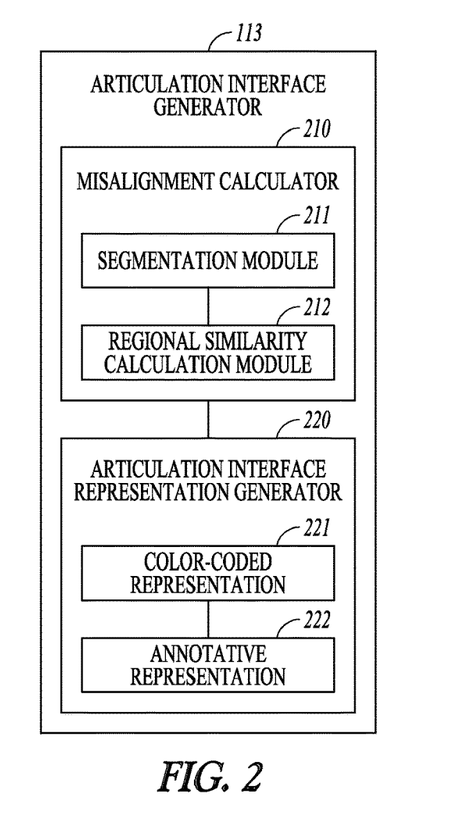
FIG. 2 is a block diagram that illustrates an example of an articulation interface generator in a prosthesis alignment and positioning system.

FIG. 2 is a block diagram that illustrates an example of an articulation interface generator 113. The articulation interface generator 113 can include a misalignment calculator 210 and an articulation interface representation generator 220. The misalignment calculator 210, coupled to the user input receiver 111 and the model receiver module 112, can calculate a regional misalignment measure (Δ) between the target bone surface representation (X) and the prosthesis surface representation (Y), when the prosthesis model is positioned against the target bone model at a specified position.

The misalignment calculator 210 can include a segmentation module 211 and a regional similarity calculation module 212. The segmentation module 211 can partition the target bone surface representation (X) into a plurality of segments {X(i)} (i=1, 2, ..., N). Similarly, the segmentation module 211 can partition the prosthesis surface representation (Y) into a plurality of segments {Y(i)} (i=1, 2, ..., N). The correspondence between segments X(i) and Y(i) can be established based on their similar locations or morphologies on their respective surface representations.

The segments {X(i)} and {Y(i)} can be created with pre-determined size and shape irrespective of the anatomical or morphologic structures of the target bone surface or the prosthesis surface. In an example where the target bone model (X) and the prosthesis model (Y) are each represented by digital images, the segments can be sized to contain a specified number of pixels of the respective digital images. The size of the segments can determine the spatial resolution of misalignment between the two surface representations X and Y. The smaller the segments, the more of the segments created on the surface representations X or Y; and therefore a finer spatial resolution of the misalignment between X and Y. In some examples, the segments {X(i)} and {Y(i)} can be created using information including anatomical or morphologic structures of the target bone surface X or the prosthesis surface Y. The segments thus created can have non-uniform sizes or shapes, and the misalignment can therefore have a non-uniform spatial resolution of the spatial misalignment is non-uniform as well.

The regional similarity calculation module 212 can calculate regional similarity measure D(X(i), Y(i)). D(X(i), Y(i)) is a quantitative measure of the regional misalignment in shapes, morphologies, or topologies between the segments X(i) and Y(i). D(X(i), Y(i)) can be computed using features extracted from the segments X(i) and Y(i). Examples of features can include location such as coordinates in a coordinated system, an orientation, a curvature, a contour, a shape, an area, a volume, or other geometric or volumetric parameters. The features can also include one or more intensity-based parameters. The features can be extracted in the space domain, frequency domain, or space-frequency domain. In various examples, the features may include statistical measurements derived from the geometric or intensity-based parameters, such as the mean, median, mode, variance, covariance, and other second or higher order statistics.

Depending on the types of the features or the data format representing the features (such as the imaging modality or image type), different regional similarity measure D(X(i), Y(i)) can be used. In an example, the extracted features are coordinates of X(i) and Y(i) in a common coordinated system. The regional similarity measure D(X(i), Y(i)) can be computed as one of L1 norm, L2 norm (Euclidian distance), infinite norm, or other distance measurements in the normed vector space. The regional similarity measure D(X(i), Y(i)) can also be computed as signed distance between X(i) and Y(i) along a particular direction in the coordinated system. The sign of D(X(i), Y(i)) can indicate the relative position of Y(i) with respect to X(i). For example, the distance is positive if Y(i) is above X(i) by at least a specified amount, or negative if Y(i) is below X(i) by at least a specified amount. In some examples, the extracted features are intensity-based features; and the similarity measure D(X(i), Y(i)) can be computed as correlation coefficient, mutual information, or ratio image uniformity.

The articulation interface representation generator 220 can generate an articulation interface representation (S) using the regional similarity measure D(X(i), Y(i)). The articulation interface representation (S) can be a computer-generated 2D or 3D image with a size comparable to the size of the target bone surface or the size of the prosthesis surface. The articulation interface representation (S) can be segmented in a fashion similar to the segmentation of the target bone surface and the prosthesis surface. For example, the articulation interface representation (S) can be segmented into a plurality of segments {S(i)} for i=1, 2, ..., N, with the segment S(i) corresponding to the segment of the target bone surface representation X(i) and the segment of the prosthesis surface representation Y(i).

The articulation interface representation (S) can be either one or a combination of a color-coded representation 221 or an annotative representation 222. In color-coded representation 221, a specified color C(i) can be rendered to segment S(i) of articulation interface representation according to the similarity measure D(X(i), Y(i)), such as when D(X(i), Y(i)) exceeds a specified threshold or falls within a specified range. In one embodiment, the color-coded representation 221 can include at least a first color $C_a$ and a different second color $C_b$. In an example, $C_a$ and $C_b$ can be two colors having different hues, such as green and red. The color $C_a$ can be used to denote a misalignment in a first direction between a portion of the prosthesis surface and a corresponding portion of the target bone surface. The color $C_b$ can be used to denote a misalignment in a different second direction between a portion of the prosthesis surface and a corresponding portion of the target bone surface. In an example where the similarity measure D(X(i), Y(i)) is computed as a signed distance between X(i) and Y(i) along a particular direction in the coordinated system, $C_a$ is rendered to segment S(i) if D(X(i), Y(i)) is positive, which indicates that the segment of the prosthesis surface Y(i) is above the corresponding segment of the target bone surface X(i) by at least a specified amount; and $C_b$ is rendered to segment S(j) if D(X(j), Y(j)) is negative, which indicates that the segment of the prosthesis surface Y(j) is below the corresponding segment of the target bone surface X(j) by at least a specified amount.

The color-coded representation 221 can additionally include a third color $C_0$ different from the first color $C_a$ and the second color $C_b$, such as a color having different hue than $C_a$ or $C_b$. $C_0$ can be rendered to a segment S(k) of the articulation interface representation if the segment of the prosthesis surface Y(k) is within a specified range relative to, and not substantially misaligned with, the segment of the target bone surface X(k). For example, when $\|D(X(k), Y(k))\|$ is smaller than a specified threshold, the segments X(k) and Y(k) are regarded as substantially aligned to each other; and color $C_0$ can be applied to the articulation interface segment S(k).

In another example, the color-coded representation 221 can include a first set of colors $\{C_a^1, C_a^2, \ldots, C_a^P\}$ and a different second set of colors $\{C_b^1, C_b^2, \ldots, C_b^Q\}$. The first set $\{C_a^1, C_a^2, \ldots, C_a^P\}$ can differ from the second set $\{C_b^1, C_b^2, \ldots, C_b^Q\}$ by some easily identifiable characteristic such as hues. The colors within a set can share a common and easily identifiable characteristic such as having the same hue, but differ from each other in at least one color parameter such as saturation or brightness. In an example, the first set includes green colors with different saturation or brightness $\{G^1, G^2, \ldots, G^Q\}$, and the second set includes red colors with different saturation or brightness $\{R^1, R^2, \ldots, R^P\}$.

The multiple colors in a color set can be used to differentiate various degrees of misalignment on a particular direction. Each of the first set of colors, such as $C_a^P$, indicates Y(i) being misaligned in a first direction with X(i) by a specified amount. Likewise, each of the second set of colors, such as $C_b^q$, indicates Y(i) being misaligned in a second direction with X(i) by a specified amount. The degree of misalignment can be represented by the magnitude of D(X(i), Y(i)), that is, $\|D(X(i), Y(i))\|$. Color $C_a^P$ is rendered to segment S(i) if D(X(i), Y(i)) is positive and $\|D(X(i), Y(i))\|$ is within a first specified range. Likewise, color $C_b^q$ is rendered to segment S(j) if D(X(j), Y(j)) is negative and $\|D(X(i), Y(i))\|$ is within a second specified range.

In annotative representation 222, a specified annotation A(i) can be applied to a segment of the articulation interface representation, S(i), according to the similarity measure D(X(i), Y(i)). A(i) can be in one or a combination of different forms including signs, labels, lines, texts, or any other markings. In an example, for a region in the articulation interface representation, a first annotation $A_a$ can be applied therein if a portion of the prosthesis surface misaligns in a first direction with a corresponding portion of the target bone surface, or a second different annotation $A_b$ can be applied if a portion of the prosthesis surface misaligns in a second direction with a corresponding portion of the target bone surface. For example, similar to the color-coded representation 211, if the similarity measure $D(X(i), Y(i))$ is computed as a signed distance between $X(i)$ and $Y(i)$ along a particular direction in the coordinated system, $A_a$ can be applied to segment $S(i)$ if $D(X(i), Y(i))$ is positive, which indicates that the prosthesis surface $Y(i)$ is above the corresponding segment of the target bone surface $X(i)$ by at least a specified amount. $A_b$ can be applied to segment $S(j)$ if $D(X(j), Y(j))$ is negative, which indicates that the prosthesis surface $Y(j)$ is below the corresponding segment of the target bone surface $X(j)$. Similar to a color set, the annotative representation 222 can include a first set of annotations $\{A_a^1, A_a^2, \ldots, A_a^P\}$ and a different second set of annotations $\{A_b^1, A_b^2, \ldots, A_b^Q\}$ to differentiate various degrees of misalignment on a particular direction. The first set $\{A_a^1, A_a^2, \ldots, A_a^P\}$ can differ from the second set $\{A_b^1, A_b^2, \ldots, A_b^Q\}$ by some easily identifiable characteristic such as labels or signs.

The annotations within a set can share a common and easily identifiable characteristic such as having the same labels or signs (e.g., a "+" label), but differ from each other in at least one characteristic such as font, size, or weight of the labels. An annotation can be selected from the first or the second set and applied to segment $S(i)$ according to $D(X(i), Y(i))$. For example, an annotation $A_a^P$ (e.g., a size-10 "+" label) can be rendered to a segment $S(i)$ if $D(X(i), Y(i))$ is positive and $\|D(X(i), Y(i))\|$ is within a specified range. Likewise, a different annotation $A_b^q$ (e.g., a size-8 "–" label) can be rendered to a segment $S(j)$ if $D(X(j), Y(j))$ is negative and $\|D(X(i), Y(i))\|$ is within a specified range. The same annotation can be applied to the entire region of segment $S(i)$, or a partial region of $S(i)$ such as borders of $S(i)$ between $S(i)$ and its neighboring segments. In some examples, the annotation is applied to the borders between the regions having different directions of misalignment, such as the borders between a region of positive misalignment (i.e., prosthesis surface is above the target bone surface) and a neighboring region of negative misalignment (i.e., prosthesis surface is below the target bone surface).

In various examples, the segment $S(i)$ may be rendered a blend of color-coded representation 221 and annotative representation 222. For example, a segment $S(i)$ can be green with annotative markings "+" on the borders of $S(i)$. In another example, the segment $S(i)$ can be filled with green-colored labels "+" on the entirety of $S(i)$.

Although articulation interface representation generator 220 is shown to include one or both of color-coded representation 221 and annotative representation 222 are illustrated in FIG. 2, other visual representations can also be included in the articulation interface representation for the purpose of differentiating various spatial relationships between the segments $Y(i)$ and $X(i)$. For example, the color-coded representation 221 can be augmented or substituted with a pattern, a texture, or an effect such as shadow, edge enhancement, lightning, or gradient.

FIGS. 3A-D illustrate examples of an articulation interface representation 350 between a femoral surface and a prosthesis surface, when a prosthesis model 320 is positioned against a distal femur model 310 at a first position. The distal femur model 310 includes a femoral surface representation 312, and the prosthesis model 320 includes a prosthesis surface representation 322. The models 310 and 320, the surface representations 312 and 322, and the articulation interface representation 350 can be generated before and during the surgery and prosthesis placement, and displayed on a monitor, such as by using the prosthesis alignment system 100 or its various embodiments discussed in this document.

Figure 3A:
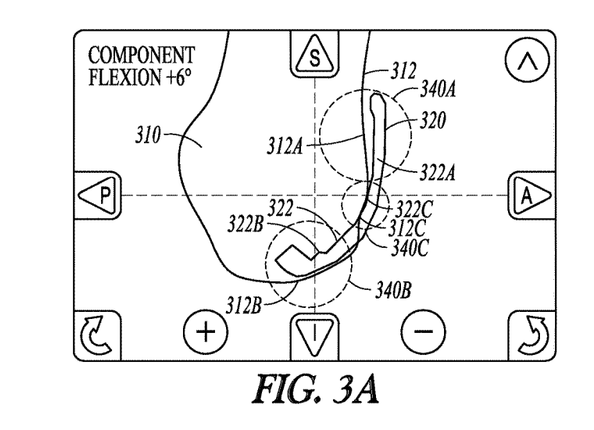
FIGS. 3A-D illustrate examples of articulation interface representations between a femoral surface and a prosthesis surface at one position of the prosthesis.

FIG. 3A illustrates the position and orientation of the prosthesis model 320 relative to the femoral model 310, when the two models are positioned against each other. The femoral model 310 and the femoral surface representation 312 each includes a data set of shape data, appearance data, or data representing other morphological characteristics of the distal femur or the femoral surface, respectively. The shape data may include geometric characteristics such as landmarks, surfaces, boundaries of three-dimensional images objections. The appearance data may include both geometric characteristics and intensity information.

The prosthesis model 320 and the prosthesis surface representation 322 each includes a data set data having a data format or modality comparable to the distal femur model 310 and the femoral surface representation 312. As illustrated in FIG. 3A, the femoral model 310 and the femoral surface representation 312 are represented as computer-simulated 2D contour models of the distal femur and the femoral surface. Similarly, the prosthesis model 320 and the prosthesis surface representation 322 are represented as computer-simulated 2D contour models.

The position of the prosthesis model 320 relative to the femoral model 310, or the position of the prosthesis surface representation 322 relative to the femoral surface representation 312, can be described using angles of flexion or extension. A wider angle indicates a higher degree of misalignment between various portions of the prosthesis surface representation 322 and the corresponding portions of the femoral surface representation 312. As illustrated in FIG. 3A, three regions of misalignment can be identified: region 340A where the portion 322A of the prosthesis surface representation is above or "outside" the corresponding portion 312A of the femoral surface representation; region 340B where the portion 322B of the prosthesis surface representation is below or "inside" the corresponding portion 312B of the femoral surface representation; and regions 340C where the portion 322C of the prosthesis surface representation is substantially aligned with or "matches" the portion 312C of the femoral surface representation.

Figure 3B:
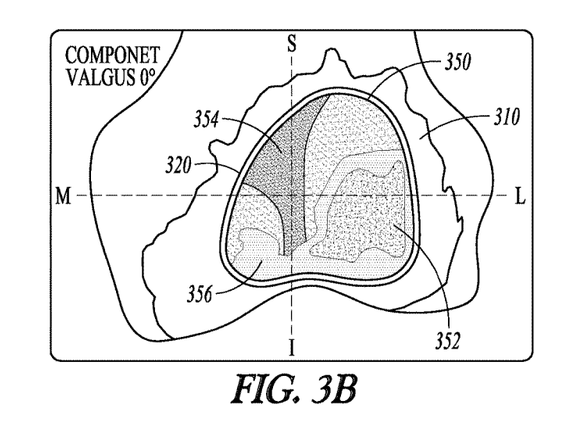
Figure 3C:
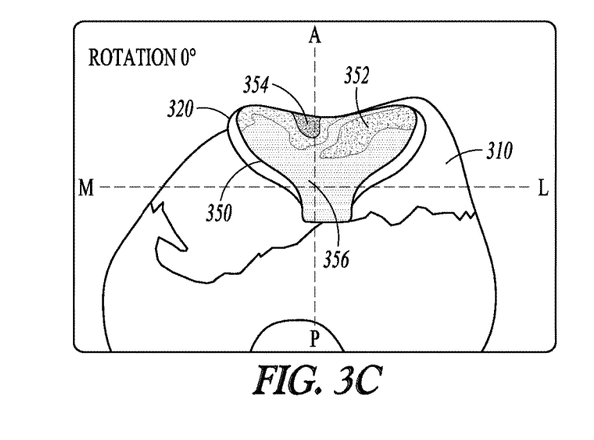
Figure 3D:
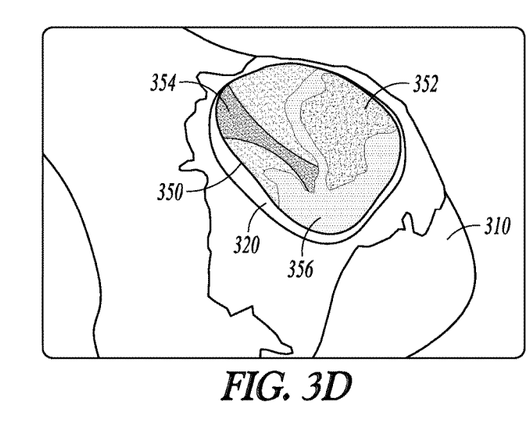

FIGS. 3B-D illustrate different angles of views of the distal femur model 310, the prosthesis model 320 positioned against the distal femur model 310, and the articulation interface representation 350 disposed over the prosthesis model 320. In particular, FIG. 3B illustrates a top view, FIG. 3C illustrates a side view, and FIG. 3D illustrates a view at a specified angle. As illustrated in FIGS. 3B-D, the articulation interface representation 350 is a color-coded representation that includes three base colors to represent three types of relative positions between various portions of the prosthesis surface representation 322 and the corresponding portions of the femoral surface representation 312. Alternatively, the articulation interface representation 350 can be a black-and-white or grayscale representation. In a grayscale representation, various shades of gray would be used to illustrate the articulation interface representation.

The FIGS. 3B-D are shown in grayscale for ease of viewing. Corresponding to region 340A, a first color is rendered to region 354 to indicate the portion 322A of the prosthesis surface representation is above or "outside" the corresponding portion 312A of the femoral surface representation. As shown in FIGS. 3B-3D, the first color can include a dark shade pattern. In another example, the first color can include green. Corresponding to region 340B, a second color is rendered to region 352 to indicate the portion 322B of the prosthesis surface representation is below or "inside" the corresponding portion 312B of the femoral surface representation. As shown in FIGS. 3B-3D. the second color can include a spotted pattern. In another example, the second color can include red. Corresponding to region 340C, a third color is rendered to region 356 to indicate the portion 322C of the prosthesis surface representation is substantially aligned with the corresponding portion 312C of the femoral surface representation. As shown in FIGS. 3B-3D. the third color can include a dotted pattern. In another example, the third color can include gray. In yet another example, different colors, shades, textural representations, grays, black and white coloring, or the like can be used to represent different regions.

For a particular colored region such as 352, 354 or 356, variations of the base color rendered to that region can be applied to sub-regions within the colored region to differentiate variations in regional similarities such as the distance between the portions of the articulation surface and the sub-portions of the femoral surface along a particular direction in the coordinated system. For example, as illustrated in FIG. 3A, within the region 340A, the distance between 322A and 312A at different sub-regions varies. Accordingly, as shown in FIGS. 3B-D, the first color with higher saturation or lower brightness (e.g., darker) can be rendered to the sub-regions of the region 354 where the dissimilarity or distance between 322A and 312A is greater than other areas of 354.

The articulation interface representation 350 includes three annotations that represent three types of relative positions between various portions of the prosthesis surface representation 322 and the corresponding portions of the femoral surface representation 312. As illustrated in FIGS. 3B-D, the three annotated regions 352, 354 and 356 indicate the prosthesis surface representation is below, above, or substantially aligned with the corresponding portion of the femoral surface representation, respectively.

FIG. 4A-D illustrate examples of articulation interface representation 450 between a femoral surface 312 and a prosthesis surface 322, when a prosthesis model 320 is positioned against a distal femur model 310 at a second position different than the first position as shown in FIGS. 3A-D. The change from the position as shown in FIGS. 3A-D to a different position as shown in FIGS. 4A-D can be achieved by processing a user command such as via the user input module 121. The user command can also selectively scale, translate, rotate, or perform any combinations of manipulations over one or both of the target bone model 310 and the prosthesis model 320.

Figure 4A:
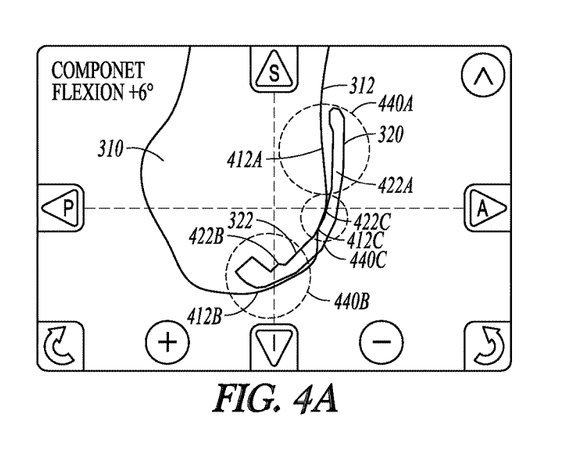
FIGS. 4A-D illustrate examples of articulation interface representations between a femoral surface and a prosthesis surface at another position of the prosthesis.

Compared to that in FIG. 3A, the flexion angle shown in FIG. 4A is wider, and the prosthesis surface representation 322 is more misaligned with the femoral surface representation 312. The resulting three regions of misalignment 440A-C therefore have different sizes and shapes than the regions 340A-C. For example, there is a higher degree of misalignment in the "above" direction between the surfaces 422A and 412A in regions 440A than between the surfaces 322A and 312A in regions 340A. Likewise, there is a higher degree of misalignment in the "below" direction between the surfaces 422B and 412B in region 440B than between the surfaces 322B and 312B in region 340B. Additionally, the substantial alignment region 440C has a smaller size than the region 340A.

Figure 4B:
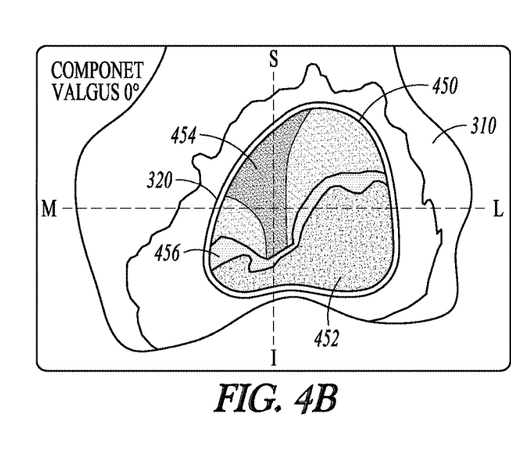
Figure 4C:
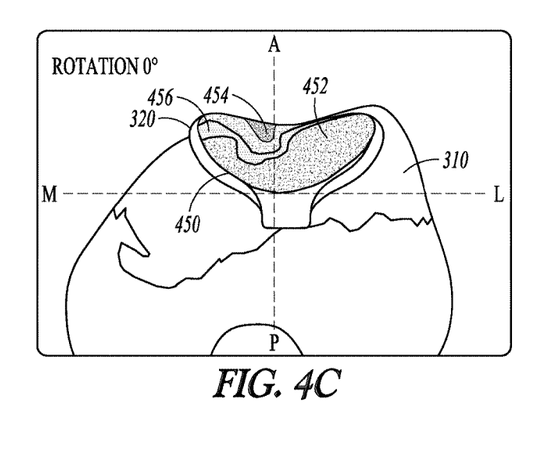
Figure 4D:
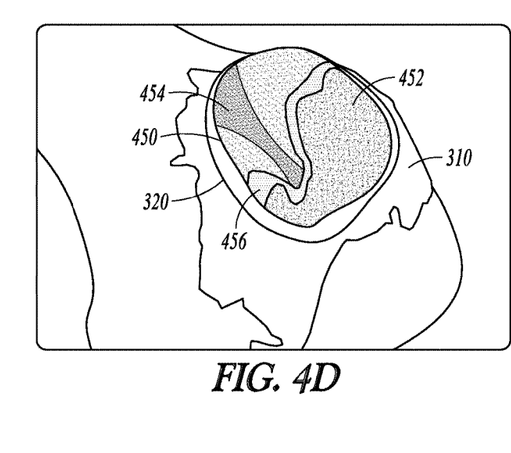

Alternatively, as illustrated in FIGS. 4B-D, the articulation interface representation 450 can be a black-and-white or grayscale representation. The FIGS. 4B-4D are shown in grayscale for ease of viewing. Consistent with the changes in regional misalignment shown in FIG. 4A, FIGS. 4B-D each represent the changes in size and shape of a second colored region 452 corresponding to region 440B, a first colored region 454 corresponding to region 440A, and a third colored region 456 corresponding to region 440C. As shown in FIGS. 4B-4D, the first, second, and third colors can include a dark shade pattern, a spotted pattern, and a dotted pattern, respectively. In another example, the first, second, and third colors can include green, red, and gray, respectively. In yet another example, different colors, shades, textural representations, grays, black and white coloring, or the like can be used to represent different regions. FIGS. 4B-D are views from different angles of the articulation interface representation 450, each including three annotations that represent three types of relative positions (above, below, or substantial alignment) between various portions of the prosthesis surface representation 322 and the corresponding portions of the femoral surface representation 312.

Variations of the base color can be applied to the sub-regions of the regions 452, 454 or 456 to differentiate within-region differences in alignment. As illustrated in FIGS. 3B-D and FIGS. 4B-D, base colors with different amount of saturation or brightness can be used according to the similarity such as the distance between the portions of the surface 312 and the corresponding portions of surface 322 along a particular direction in a coordinated system. For example, corresponding to greater distance between 422A and 412A in region 440A compared to that between 322A and 312A in region 340A, a wider sub-region within the region 454 can be rendered the first color with higher saturation or lower brightness (e.g., darker). Likewise, corresponding to greater distance between 422B and 412B in region 440B compared to that between 322B and 312B in region 340B, a wider sub-region within the region 452 can be rendered the second color with lower saturation or higher brightness (e.g., brighter). Alternatively, when the articulation interface representation 350 or 450 is a black-and-white representation, variations of the annotation can be applied to the sub-regions of the regions 452, 454 or 456 to differentiate within-region differences in alignment. For example, as illustrated in FIGS. 3B-D and FIGS. 4B-D, a darker color, or a pattern with markings (e.g., dots) with a higher density can be used to indicate greater distance between the portions of the surface 312 and the corresponding portions of surface 322 along a particular direction in a coordinated system.

Figure 5:
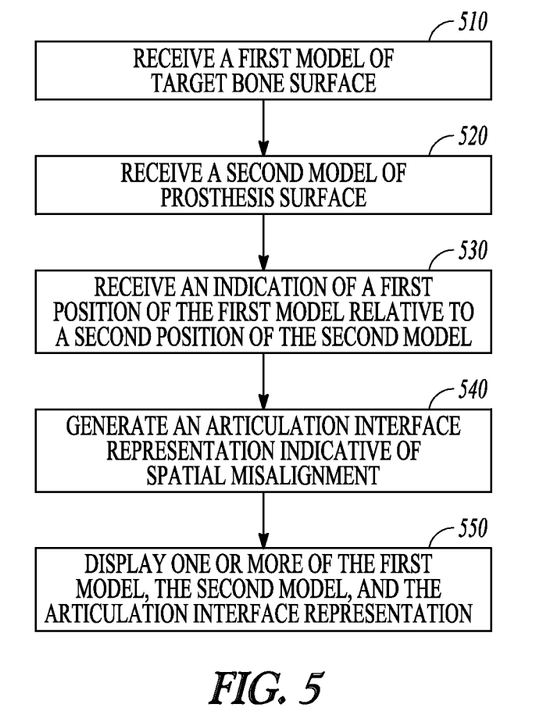
FIG. 5 is a flowchart that illustrates an example of a method for aligning a prosthesis surface to a target bone surface.

FIG. 5 is a flowchart that illustrates an example of a method 500 for aligning a prosthesis surface to a target bone surface. The method 500 can be used in orthopedic surgeries such as joint resurfacing arthroplasty. In an embodiment, the system 100, including its various embodiments discussed in this document, can perform method 500, including its various embodiments discussed in this document.

The method 500 begins with receiving a target bone model at 510, such as by using a model receiver module 112. The target bone model can include an articulation surface of the target bone. Examples of the target bone can include an acetabulum, a proximal or distal extremity of a femur, a proximal or distal extremity of a tibia, or any other bone in a body. The target bone can be surgically prepared to host a prosthesis component. At least a portion of the target bone, such as the articulation surface, undergoes surgical alteration, repair, or resection, such that the prosthesis can be securely placed against the target bone to replace the articulation surface of the target bone.

The target bone model can include a data set characterizing geometric characteristics including position, shape, contour, or appearance of the target bone surface. The data set can also include intensity information. In various examples, the target bone model can include at least one medical image such as an X-ray, an ultrasound image, a computed tomography (CT) scan, a magnetic resonance (MR) image, a positron emission tomography (PET) image, a single-photon emission computed tomography (SPECT) image, or an arthrogram, among other 2D or 3D images. The target bone model can be received from a patient database, or from an imaging system or an image acquisition system. In an example, the target bone model is calculated intra-operatively by collecting a cloud of points from the target bone using an optically tracked stylus (pointer) or similar device. In this example, the surface of the target bone is obtained by a surgeon prior to enable the computing system to calculate a target bone model from the collected points. In some examples, multiple methods of creating a target bone model can be combined, such as fitting a database model to an actual bone using collected points.

At 520, a prosthesis model can be received such as by using the user input module 121. The prosthesis model includes a data set representing a surface of a prosthesis, which is sized, shaped or configured to at least partially replace the articulation surface of the target bone. The prosthesis model can be in a format of a parametric model, a statistical model, a shape-based model, a volumetric model, an elastic model, a geometric spine model, or a finite element model. In some embodiments, the prosthesis model has a data format or modality comparable to the target bone model.

At 530, information of relative positions between the target bone model and the prosthesis model is received, such as via a user input module that enables a system user to interactively select or deselect one or both of the target bone model or the prosthesis model, and alter one or more properties thereof. The received relative positions can include indication of a position of the prosthesis surface representation relative to the target bone surface representation when the prosthesis surface is positioned against the target bone surface. In an example, the position of the target bone surface representation and the position of the prosthesis surface representation can be characterized by their respective coordinates in a common coordinated system. In some examples, an indication of a change in positions of one or both of target bone surface representation and the prosthesis surface representation can be received. In addition to the indication of position change, other properties of the models that can be altered include translation, rotation, reflection, scaling, stretching, shrinking, or any other manipulations or any combination of the manipulations over one or both of the target bone model and the prosthesis model. In some examples, manipulations of the prosthesis model, such as scaling, stretching or shrinking, are restricted based on the actual prosthesics available for implant.

At 540, an articulation interface representation is generated, such as by using the articulation interface generator 113. The articulation interface representation indicates spatial misalignment between one or more portions of the prosthesis surface and the respective one or more portions of the target bone surface, when the two models are positioned against each other along a specified direction. The articulation interface representation (S) can have similar data format as the target bone surface representation (X) or the prosthesis surface representation (Y). In an example, the articulation interface representation (S) can be a computer-generated 2D or 3D image with a size comparable to the size of the target bone surface representation or the size of the prosthesis surface representation. The articulation interface representation can include a color-coded representation, an annotative representation, or other markup representations or overlays of two or more different representations to assist the surgeon in reliably positioning the prosthesis onto the target bone with improved accuracy and consistency. An alignment index can also be computed using the articulation interface representation. Example methods of generating the articulation interface representation are discussed below, such as with reference of FIG. 6.

At 550, one or more of the target bone model, the prosthesis model, and the articulation interface representation can be displayed such as on a monitor or other display module. The graphical representation of one or both of the target bone model or the prosthesis model can be overlaid with the articulation interface representation. The display module or the monitor can also interactively display the user commands such as selecting, positioning, scaling, translating, rotating, reflecting, stretching, shrinking, or any other manipulations or any combination of the manipulations over one or more the target bone model, the prosthesis model, or the articulation interface representation. Also displayed can include a plurality of specified angles of views or projections of the target bone model, the prosthesis model, or the articulation interface representation. The computed alignment index can also be displayed, which can be used by the system user to adjust relative positions of the prosthesis surface representation and the target bone surface representation to achieve a desired alignment.

Figure 6:
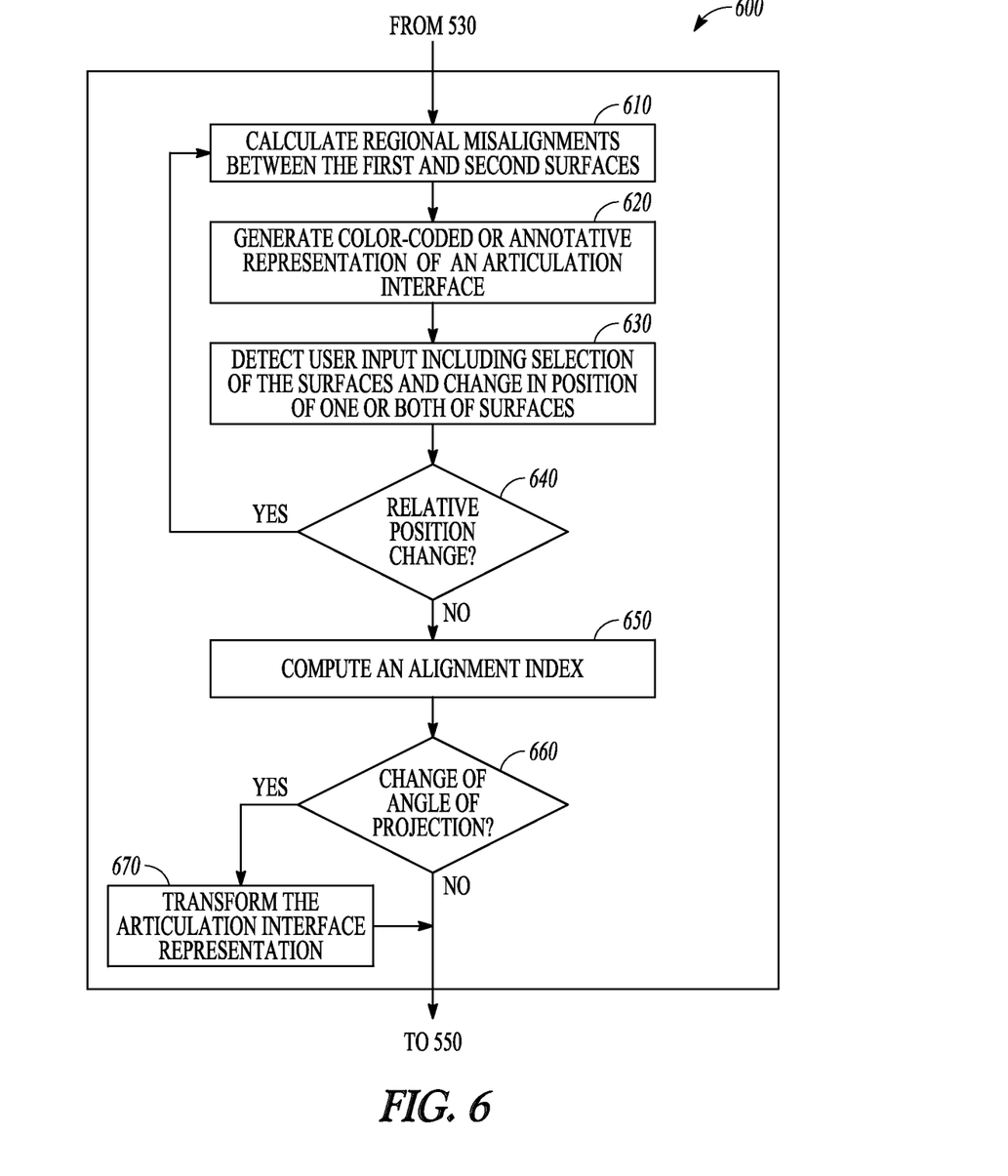
FIG. 6 is a flowchart that illustrates an example of a method for generating an articulation interface representation.

FIG. 6 is a flowchart that illustrates an example of a method 600 for generating an articulation interface representation and determining a desirable alignment between the prosthesis model and the target bone model. The method 600 can be an example of the articulation interface generation process 540 illustrated in FIG. 5.

Using the received target bone surface representation (X), the prosthesis surface representation (Y), and the indication of the relative positions between the two surface representations, such as those provided in 510-530, regional misalignments (Δ) between various regions of the two surfaces can be calculated at 610, such as by using the misalignment calculator 210. The regional misalignment (Δ) can be a quantified representation of the discrepancies between the shapes, morphologies, or topologies of multiple regions created on the target bone surface representation (X) and the prosthesis surface representation (Y). In an embodiment, the regional misalignment (Δ) can be computed by partition the target bone surface representation (X) into a plurality of segments {X(i)} (i=1, 2, . . . , N), and in a similar fashion portioning the prosthesis surface representation (Y) into a plurality of segments {Y(i)} (i=1, 2, . . . , N). The segments, {X(i)} and {Y(i)}, can be created with pre-determined size and shape irrespective of the anatomical or morphologic structures of the target bone surface or the prosthesis surface. For example, when the target bone model (X) and the prosthesis model (Y) are each represented by digital images, segments {X(i)} and {Y(i)} can be sized to contain a specified number of pixels of the respective digital images. Features, such as geometric features, morphological features, statistical features, or intensity-based features, can be extracted from each target bone surface segment X(i) and the corresponding prosthesis surface segment Y(i), and a regional similarity measure D(X(i), Y(i)) between the segments X(i) and Y(i) can be computed. Examples of D(X(i), Y(i)) can include L1 norm, L2 norm (Euclidian distance), infinite norm, or other distance-based measures in a vector space; correlation coefficient, mutual information, or ratio image uniformity. $D(X(i), Y(i))$ can also be computed as signed distance between $X(i)$ and $Y(i)$ along a particular direction in the coordinated system. The sign of $D(X(i), Y(i))$ can indicate the relative position of $Y(i)$ with respect to $X(i)$ when $Y(i)$ and $X(i)$ are positioned against each other. For example, the distance is positive if $Y(i)$ is above $X(i)$ by at least a specified amount, and negative if $Y(i)$ is below $X(i)$ by at least a specified amount.

At 620, a visual representation of an articulation interface can be generated using the calculated regional misalignments. The visual representation can include a color-coded representation, an annotative representation, or a combination of the two such as a colored annotation. The articulation interface representation (S) can be a computer-generated 2D or 3D image with a size and shape comparable the target bone surface representation (X) or the prosthesis surface representation (Y). Using a similar segmentation process, the articulation interface representation (S) can be segmented into a plurality of segments $\{S(i)\}$ for $i=1, 2, \ldots N$, with the segment $S(i)$ corresponding to the segment of the target bone surface representation $X(i)$ and the segment of the prosthesis surface representation $Y(i)$.

In a color-coded representation, a specified color, $C(i)$, can be rendered to a segment of the articulation interface representation, $S(i)$, if the similarity measure $D(X(i), Y(i))$ meets a specified criterion, such as exceeding a specified threshold or falling within a specified range. In an example where the similarity measure $D(X(i), Y(i))$ is computed as a signed distance between $X(i)$ and $Y(i)$ along a particular direction in the coordinated system, a first color $C_a$ (e.g., a green color) can be rendered to segment $S(i)$ if $D(X(i), Y(i))$ is positive, which indicates that the segment $Y(i)$ is misaligned in a first direction relative to the corresponding segment $X(i)$, such as being positioned above $X(i)$ by at least a specified amount. A different second color $C_b$ (e.g., a red color) can be rendered to a segment $S(j)$ if $D(X(j), Y(j))$ is negative, which indicates that the segment $Y(j)$ is in a different second direction relative to the corresponding segment $X(j)$, such as being positioned below $X(j)$ by at least a specified amount. Additionally, a third color $C_0$ (e.g., a gray color), different from $C_a$ and $C_b$, can be rendered to a segment $S(k)$ if the magnitude of $D(X(j), Y(j), \|d(X(i), Y(i))\|$, is below a specified threshold, which indicates that the prosthesis surface segment $Y(k)$ is substantially aligned with the corresponding target bone surface segment $X(k)$.

In some examples, a set of colors $\{C_a^1, C_a^2, \ldots, C_a^P\}$ can be used to represent various degrees of misalignment in the first direction between $X(i)$ and $Y(i)$, such as when $Y(i)$ is positioned above $X(i)$. Similarly, a different set of colors $\{C_b^1, C_b^2, \ldots, C_b^Q\}$ can be used to represent various degrees of misalignment in the second direction between $X(i)$ and $Y(i)$, such as when $Y(i)$ is positioned below $X(i)$. A correspondence, such as a lookup table, between the multiple colors in the color sets and the value ranges of $D(X(j), Y(j))$ can be established. The similarity measure $D(X(i), Y(i))$ for a segment $S(i)$ can be compared to multiple threshold values or the range values, and one color can be selected from the color sets $\{C_a^1, C_a^2, \ldots, C_a^P\}$ or $\{C_b^1, C_b^2, \ldots, C_b^Q\}$, and rendered to the segment $S(i)$. In various examples, the color-coded representation can be augmented or substituted by a pattern, a texture, or a style with effects such as shadow, edge enhancement, lightning, or gradient.

In an annotative representation, a specified annotation, such as one or a combination of different forms of annotations including signs, labels, lines, texts, or any other markings, can be rendered to an articulation interface representation segment $S(i)$ according to the similarity measure $D(X(i), Y(i))$. Similar to the color-coded representation, a first annotation $A_a$ can be rendered to segment $S(i)$ if $D(X(i), Y(i))$ is positive, which indicates that the prosthesis surface segment $Y(i)$ is above the corresponding target bone surface segment $X(i)$ by at least a specified amount. A different second annotation $A_b$ can be rendered to a different segment $S(j)$ if $D(X(j), Y(j))$ is negative, which indicates that the segment $Y(j)$ is below the segment $X(j)$ by at least a specified amount. Additionally, a third annotation $A_0$ can be rendered to a segment $S(k)$ if $\|D(X(i), Y(i))\|$ is below a specified threshold, indicating the prosthesis surface segment $Y(k)$ is substantially aligned with the target bone surface segment. Multiple annotations in a annotation set can be used to differentiate various degrees of misalignment between segment $Y(i)$ and $X(i)$, such as by comparing $D(X(i), Y(i))$ to multiple threshold values or range values, a similar method as discussed above in color-coded representations.

At 630, a user input can be received such as via a user input module. The user input can include an indication of selecting or deselecting one or more of the target bone surface representation, the prosthesis surface representation, or the articulation interface representation. The user input can also include change in positions of one or more of target bone surface representation, the prosthesis surface representation, or the articulation interface representation.

Relative position change between the target bone model and the prosthesis model is then detected at 640. In an example, both the target bone model and the prosthesis model are selected, such that their positions are concurrently changed while the relative positions or orientations between them are preserved. In another example, only one of the target bone model or the prosthesis model is selected and repositioned, and a relative position change is detected at 640.

If a relative change between the models is detected at 640, then at least some segments of the articulation interface can have different regional similarity measure $D(X(i), Y(i))$. The regional misalignments can then be recalculated at 610. However, if no relative change is detected at 640, then an alignment index is computed at 650. The alignment index can be a measure of an overall disconformity between the target bone surface representation and the prosthesis surface representation. In an example, L can be computed as a square-root of the sum of squared regional similarity measures among all segments. The alignment index can also include statistical measurements of disconformities such as maximum, minimum, average, median, range, histogram, or other distributional representations of the disconformities among multiple regions of the target bone surface and the articulation interface.

The user input detected at 630 can also include an indication of the angles of view or projections of the target bone model, the prosthesis model, or the articulation interface representation. For example, as illustrated in FIGS. 3A-D and FIGS. 4A-D, multiple angles of views of a computer-generated 3D image of the distal femur model and the associated femoral surface representation can be generated and displayed, including a top view, a side view, a front view, or and at any perspective obtained after specified rotation. If no change of viewing angle is detected at 660, then the generated articulation interface representation can be displayed at 550. However, if a change of viewing angle (such as by rotating a model) is detected at 660, then the articulation interface representation can be transformed at 670 in accordance with the change of angle of view. The transformed articulation interface can be displayed at 550.

Figure 7:
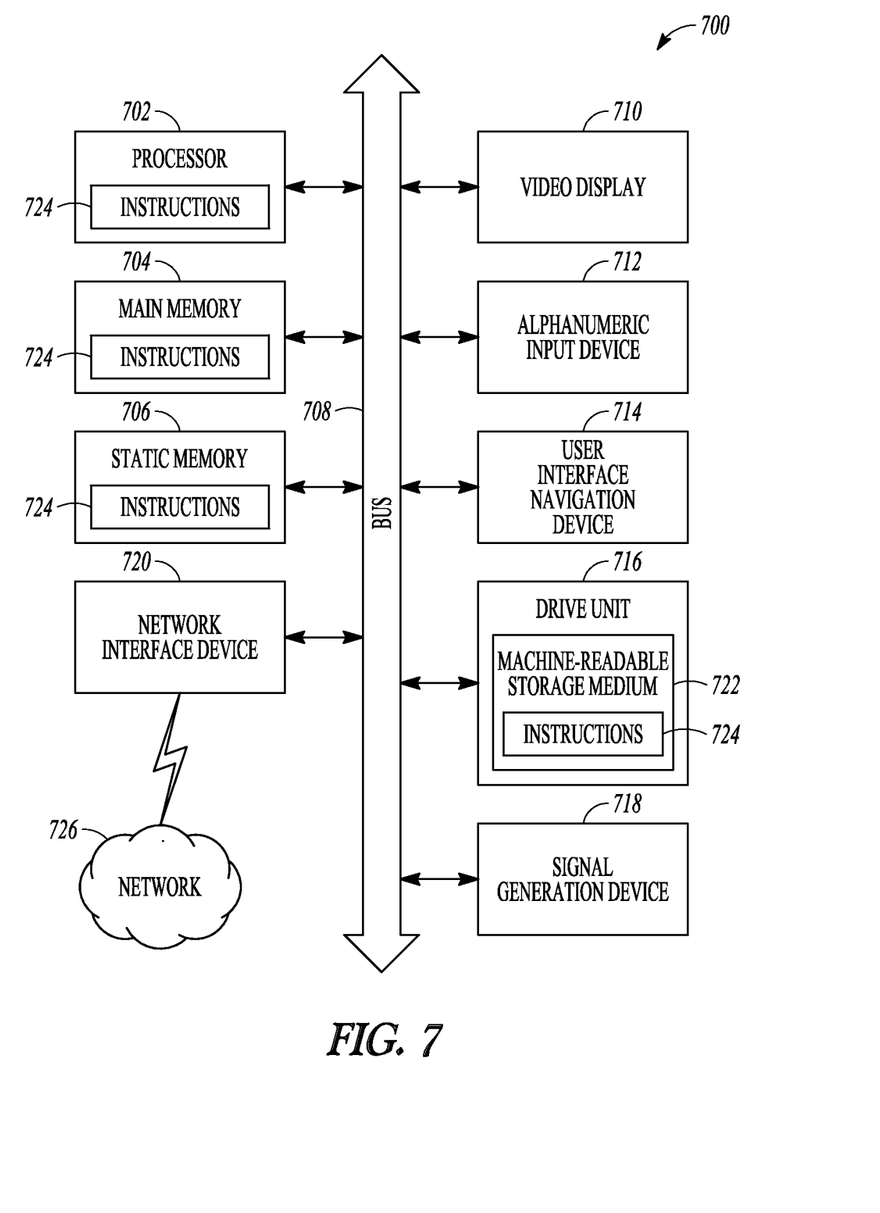
FIG. 7 is a block diagram that illustrates an example of a computer system within which instructions for causing the computer system to perform prosthesis alignment may be executed.

FIG. 7 is a block diagram that illustrates an example of a machine in the form of a computer system 700 within which instructions, for causing the computer system to perform any one or more of the methods discussed herein, may be executed. In various embodiments, the machine can operate as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 702 (such as a central processing unit (CPU), a graphics processing unit (GPU), or both), a main memory 704 and a static memory 706, which communicate with each other via a bus 708. The computer system 700 may further include a video display unit 710 (such as a liquid crystal display (LCD) or a cathode ray tube (CRT)), an alpha-numeric input device 712 (such as a keyboard), a user interface (UI) navigation device (or cursor control device) 714 (such as a mouse), a disk drive unit 716, a signal generation device 718 (e.g., a speaker) and a network interface device 720.

The disk drive unit 716 includes a machine-readable storage medium 722 on which is stored one or more sets of instructions and data structures (e.g., software) 724 embodying or used by any one or more of the methods or functions described herein. The instructions 724 may also reside, completely or at least partially, within the main memory 704, static memory 706, and/or within the processor 702 during execution thereof by the computer system 700, the main memory 704 and the processor 702 also constituting machine-readable media. In an example, the instructions 724 stored in the machine-readable storage medium 722 include instructions causing the computer system 700 to receive target bone model such as a first data set representing a target bone surface, and to receive a prosthesis model such as a second data set representing a prosthesis surface. The prosthesis component can be configured to be positioned against the target bone such as to partially replace the articulation surface of the target bone. The instructions 724 can also store the instructions 724 that cause the computer system 700 to generate an articulation interface representation such as one or a combination of a color-coded representation, an annotative representation, or other markup representations or overlays of two or more different representations using both the target bone surface representation and the prosthesis surface representation, and calculate an alignment index that represents overall disconformity between the target bone surface and the articulation interface.

To direct the computer system 700 to generate the articulation interface representation, the machine-readable storage medium 722 may further store the instructions 724 that cause the computer system 700 to receive a user input including an indication of a change in position of one or both of the prosthesis surface model or the target bone surface model, and to update the articulation interface representation in response to the user input including the indication of the change in relative positions between the prosthesis surface model or the target bone surface model. The instructions in the machine-readable storage medium 722 may also cause the computer system 700 to generate representation illustrating one or more of the target bone model, the prosthesis model, and the articulation interface representation.

While the machine-readable medium 722 is shown in an example embodiment to be a single medium, the term "machine-readable medium" may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

In various examples, the instructions 724 may further be transmitted or received over a communications network 726 using a transmission medium. The instructions 724 may be transmitted using the network interface device 720 and any one of a number of well-known transfer protocols (e.g., HTTP). Examples of communication networks include a LAN, a WAN, the Internet, mobile telephone networks, plain old telephone (POTS) networks, and wireless data networks (e.g., Wi-Fi and WiMAX networks). The term "transmission medium" shall be taken to include any intangible medium that is capable of storing, encoding or carrying instructions for execution by the machine, and includes digital or analog communications signals or other intangible media to facilitate communication of such software.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
a processor unit, configured to:
receive a first model including a first data set representing a first surface of a target bone and a second model including a second data set representing a second surface of a prosthesis, the first surface including an articulation surface of the target bone, the prosthesis configured to at least partially replace the articulation surface,
calculate one or more regional misalignments between the first model and the second model, wherein calculating the one or more regional misalignments comprises:
segmenting the first model into a first plurality of segments,
segmenting the second model into a second plurality of segments,
determining corresponding segments in the first plurality of segments and the second plurality of segments based on location or morphological features of surface representations of the first plurality of segments and the second plurality of segments,
extracting one or more features from the corresponding segments, and
calculating a similarity measure between corresponding segments in the first plurality of segments and the second plurality of segments based on the extracted one or more features of the corresponding segments, and
generate a visual articulation interface representation based on the one or more regional misalignments, the articulation interface representation indicative of one or more portions of the second surface being spatially misaligned with respective one or more portions of the first surface when the second model is positioned against the first model; and
a graphical user interface unit, including:
a user input module configured to receive a user input including an indication of a change in position of one or both of the first and second models, and
a display module coupled to the user input module and the processor unit, the display module configured to display one or more of the first model, the second model, and the articulation interface representation.

2. The system of claim 1, wherein the processor unit is configured to receive the first and second models, the first model including a first three-dimensional graphical representation of the first surface of a target bone, the second model including a second three-dimensional graphical representation of the second surface of the prosthesis.

3. The system of claim 1, wherein the processor unit is configured to generate a plurality of specified angles of views of at least one of the first model, the second model, and the articulation interface representation.

4. The system of claim 1, wherein the processor unit is configured to generate the articulation interface representation including a color-coded representation, the color-coded representation including a first color associated with a first portion of the second surface being misaligned in a first direction with a first portion of the first surface, and a different second color associated with a second portion of the second surface being misaligned in a second direction with a second portion of the first surface.

5. The system of claim 4, wherein the color-coded representation includes a first set of colors each associated with a first portion of the second surface being misaligned in a first direction with a first portion of the first surface by a first specified amount, and a second set of colors each associated with a second portion of the second surface being misaligned in a second direction with a second portion of the first surface by a second specified amount.

6. The system of claim 4, wherein the color-coded representation further includes a third color different from the first and second colors, the third color associated with a third portion of the second surface being disposed within a third specified range relative to, and not misaligned with, a third portion of the first surface.

7. The system of claim 1, wherein the processor unit is configured to generate the articulation interface representation including an annotative representation, the annotative representation including a first marking associated with a first portion of the second surface being misaligned in a first direction with a first portion of the first surface, and a different second marking associated with a second portion of the second surface being misaligned in a second direction with a second portion of the first surface.

8. The system of claim 1, wherein the processor unit is configured to update the articulation interface representation in response to the user input including the indication of the change in position of one or both of the first and second models.

9. The system of claim 1, wherein the processor unit is further configured to compute an alignment index using the articulation interface representation, and to determine a desirable alignment between the first and second surfaces in response to the alignment index meeting a specified criterion.

10. The system of claim 1, wherein the user input module includes one or more pointing devices including a mouse, a trackball, or a touch screen.

11. The system of claim 1, wherein the user input module is configured to receive an indication of the change in position including a translation or a rotation of one or both of the first and second models.

12. The system of claim 1, wherein the user input module includes a user input interface configured to receive a selection between the first and second models, and to receive a change of position of the selected model relative to the other model.

13. The system of claim 12, wherein the user input interface is configured to receive a concurrent change of positions of both the first and second models with preserved relative position between the first and second models.

14. The system of claim 1, wherein the display module is configured to graphically display at least one of the first or the second models overlaid with the articulation interface representation.

15. A method of aligning a prosthesis surface to a target bone surface, the method comprising:
receiving a first model including a first data set representing a first surface of a target bone, the first surface including an articulation surface of the target bone;
receiving a second model including a second data set representing a second surface of a prosthesis, the prosthesis configured to at least partially replace the articulation surface;
receiving an indication of a first position of the first model relative to a second position of the second model;
calculating one or more regional misalignments between the first model and the second model, wherein calculating the one or more regional misalignments comprises:
segmenting the first model into a first plurality of segments,
segmenting the second model into a second plurality of segments,
determining corresponding segments in the first plurality of segments and the second plurality of segments based on location or morphological features of surface representations of the first plurality of segments and the second plurality of segments,
extracting one or more features from the corresponding segments, and
calculating a similarity measure between corresponding segments in the first plurality of segments and the second plurality of segments based on the extracted one or more features of the corresponding segments;
generating a visual articulation interface representation based on the one or more regional misalignments, the articulation interface representation indicative of one or more portions of the second surface being spatially misaligned with respective one or more portions of the first surface when the second model is positioned against the first model; and
displaying on a display module one or more of the first model, the second model, and the articulation interface representation.

16. The method of claim 15, wherein receiving the indication of the first and second positions includes receiving an indication of a change in position of one or both of the first and second models, and wherein generating the articulation interface includes updating the articulation interface representation in response to the indication of the change in position of one or both of the first and second models.

17. The method of claim 16, wherein receiving the indication of the change in position of one or both of the first and second models includes receiving an indication of a translation or a rotation of one or both of the first and second models.

18. The method of claim 15, wherein displaying one or more of the first and second models and the articulation interface representation includes displaying at least one of the first or the second models overlaid with the articulation interface representation.

19. The method of claim 15, wherein generating the articulation interface representation includes generating a color-coded representation including a first color associated with a first portion of the second surface being misaligned in a first direction with a first portion of the first surface, and a different second color associated with a second portion of the second surface being misaligned in a second direction with a second portion of the first surface.

20. The method of claim 19, wherein generating the color-coded representation includes generating a first set of colors each associated with a first portion of the second surface being misaligned in a first direction with a first portion of the first surface by a first specified amount, and a second set of colors each associated with a second portion of the second surface being misaligned in a second direction with a second portion of the first surface by a second specified amount.

21. The method of claim 19, wherein generating the color-coded representation includes generating a third color different from the first and second colors, the third color associated with a third portion of the second surface being disposed within a third specified range relative to, and not misaligned with, a third portion of the first surface.

22. The method of claim 15, wherein generating the articulation interface representation includes generating an annotative representation including a first marking associated with a first portion of the second surface being misaligned in a first direction with a first portion of the first surface, and a different second marking associated with a second portion of the second surface being misaligned in a second direction with a second portion of the first surface.

23. The method of claim 15, further comprising computing an alignment index using the articulation interface representation, and determining a desirable alignment between the first and second surfaces in response to the alignment index meeting a specified criterion.

24. A non-transitory machine-readable storage medium including instructions that, when executed by a machine, cause the machine to:
receive a first model including a first data set representing a first surface of a target bone, the first surface including an articulation surface of the target bone;
receive a second model including a second data set representing a second surface of a prosthesis, the prosthesis configured to at least partially replace the articulation surface;
calculate one or more regional misalignments between the first model and the second model, wherein calculating the one or more regional misalignments comprises:
segmenting the first model into a first plurality of segments,
segmenting the second model into a second plurality of segments,
determining corresponding segments in the first plurality of segments and the second plurality of segments based on location or morphological features of surface representations of the first plurality of segments and the second plurality of segments,
extracting one or more features from the corresponding segments, and
calculating a similarity measure between corresponding segments in the first plurality of segments and the second plurality of segments based on the extracted one or more features of the corresponding segments;
generate a visual articulation interface representation based on the one or more regional misalignments, the articulation interface representation indicative of one or more portions of the second surface being spatially misaligned with respective one or more portions of the first surface when the second model is positioned against the first model; and
display on a display module one or more of the first model, the second model, and the articulation interface representation.

25. The machine-readable storage medium of claim 24, further comprising instructions that cause the machine to:
receive a user input including an indication of a change in position of one or both of the first and second models; and
update the articulation interface representation in response to the user input including the indication of the change in position of one or both of the first and second models.

26. The machine-readable storage medium of claim 25, wherein the instruction causing the machine to receive the indication of the change in position includes causing the machine to receive an indication of a translation or a rotation of one or both of the first and second models.

27. The machine-readable storage medium of claim 24, wherein the instruction causing the machine to display one or more of the first and second models and the articulation interface representation includes causing the machine to display at least one of the first or the second models overlaid with the articulation interface representation.

28. The machine-readable storage medium of claim 24, wherein the instruction causing the machine to generate the articulation interface representation includes causing the machine to generate a color-coded representation including a first color associated with a first portion of the second surface being misaligned in a first direction with a first portion of the first surface, and a different second color associated with a second portion of the second surface being misaligned in a second direction with a second portion of the first surface.

29. The machine-readable storage medium of claim 28, wherein the instruction causing the machine to generate the color-coded representation includes causing the machine to generate a first set of colors each associated with a first portion of the second surface being misaligned in a first direction with a first portion of the first surface by a first specified amount, and a second set of colors each associated with a second portion of the second surface being misaligned in a second direction with a second portion of the first surface by a second specified amount.

30. The machine-readable storage medium of claim 28, wherein the instruction causing the machine to generate the color-coded representation includes causing the machine to generate a third color different from the first and second colors, the third color associated with a third portion of the second surface being disposed within a third specified range relative to, and not misaligned with, a third portion of the first surface.

31. The machine-readable storage medium of claim 24, wherein the instruction causing the machine to generate the articulation interface representation includes causing the machine to generate an annotative representation including a first marking associated with a first portion of the second surface being misaligned in a first direction with a first portion of the first surface, and a different second marking associated with a second portion of the second surface being misaligned in a second direction with a second portion of the first surface.

32. The machine-readable storage medium of claim 24, further comprising an instruction causing the machine to compute an alignment index using the articulation interface representation, and to determine a desirable alignment between the first and second surfaces in response to the alignment index meeting a specified criterion.

* * * * *